US009589572B2

(12) United States Patent
Gao

(10) Patent No.: US 9,589,572 B2
(45) Date of Patent: Mar. 7, 2017

(54) STEPSIZE DETERMINATION OF ADAPTIVE FILTER FOR CANCELLING VOICE PORTION BY COMBINING OPEN-LOOP AND CLOSED-LOOP APPROACHES

(71) Applicant: Yang Gao, Mission Viejo, CA (US)

(72) Inventor: Yang Gao, Mission Viejo, CA (US)

( * ) Notice: Subject to any disclaimer, the term of this patent is extended or adjusted under 35 U.S.C. 154(b) by 11 days.

(21) Appl. No.: 14/702,687

(22) Filed: May 2, 2015

(65) Prior Publication Data

US 2015/0318001 A1 Nov. 5, 2015

Related U.S. Application Data

(60) Provisional application No. 61/988,298, filed on May 4, 2014.

(51) Int. Cl.
*A61F 11/06* (2006.01)
*G10L 21/0208* (2013.01)
*G10L 21/0216* (2013.01)

(52) U.S. Cl.
CPC *G10L 21/0208* (2013.01); *G10L 2021/02166* (2013.01)

(58) Field of Classification Search
CPC ......... G10K 2210/30; G10K 2210/301; G10K 2210/3011; G10K 2210/3012; G10K 2210/3013; G10K 2210/3014; G10K 2210/3016; G10K 2210/3018; G10K 2210/3019; G10K 2210/3021; G10K 2210/3023; G10K 2210/30231; G10K 2210/30232; G10K 2210/3025; G10K 2210/3026; G10K 2210/3027; G10K 2210/3028; G10K 2210/3029; G10K 2210/3035; G10K 2210/30351; G10K 2210/3039; G10K 2210/30391; G10K 2210/3042; G10K 2210/3045; G10K 2210/3047; G10K 2210/3049;
(Continued)

(56) References Cited

U.S. PATENT DOCUMENTS 9,172,791 B1 * 10/2015 Ayrapetian ............ H04M 3/002
2010/0004929 A1 * 1/2010 Baik ................... G10L 21/0208 704/233
2010/0241426 A1 * 9/2010 Zhang ................. G10L 21/0208 704/226

* cited by examiner

*Primary Examiner* — Leshui Zhang

(57) ABSTRACT

In accordance with an embodiment of the present invention, a noise reduction method for speech processing includes estimating a noise/interference component signal by subtracting voice component signal from a first microphone input signal wherein the voice component signal is evaluated as a first replica signal produced by passing a second microphone input signal through a first adaptive filter; a stepsize is estimated to control adaptive update of the first adaptive filter, wherein the stepsize is evaluated by combing an open-loop approach and a closed-loop approach, the open-loop approach comprising voice/noise/interference classification and SNR estimation in voice area, and the closed-loop approach comprising calculating a normalized correlation between the first replica signal and the first microphone input signal. A noise/interference reduced signal is outputted by subtracting a second replica signal from a target signal which is the first microphone input signal or the second microphone input signal, wherein the second replica signal is produced by passing the estimated noise/interference component signal through a second adaptive filter.

8 Claims, 10 Drawing Sheets

(58) Field of Classification Search
CPC ... G10K 2210/3052; G10K 2210/3054; G10K 2210/3055; G10K 2210/3056; G10K 2210/3215; G10K 2210/3216; G10K 2210/3218; G10K 2210/3221; G10K 2210/3225; H04R 2201/00; H04R 2201/003; H04R 2201/10; H04R 2201/107; H04R 2201/109; H04R 2201/34; H04R 2201/40; H04R 2201/401; H04R 2201/403; H04R 2499/00; H04R 2499/01; H04R 2499/10; H04R 2499/11; H04R 2499/13; H04R 2499/15; H04R 2410/01; H04R 2410/05; H04R 3/005
USPC ............ 381/317, 318, 320, 321, 71.1–71.12, 381/71.14, 74, 80, 78, 81, 82, 83, 84, 85, 381/86, 91, 92, 93, 94.1–94.7, 94.9, 95, 381/98, 99, 100, 101, 102, 103, 111–115, 381/119, 120, 121, 122, 123; 455/63.1, 455/501, 67.13, 570, 114.2, 135, 222, 455/223, 226.3, 278.1, 283, 296; 704/226, 233, E15.039, E19.014, 704/E21.002, E21.004, E21.005, 704/E21.006, E21.007, E21.014; 379/22.08, 392.01, 406.01–406.16; 708/172, 300–323; 700/94
See application file for complete search history.

(Prior-Art)

STEPSIZE DETERMINATION OF ADAPTIVE FILTER FOR CANCELLING VOICE PORTION BY COMBINING OPEN-LOOP AND CLOSED-LOOP APPROACHES

This application claims the benefit of U.S. Provisional Application No. 61/988,298 filed on May 4, 2014, entitled "Stepsize Determination of Adaptive Filter For Cancelling Voice Portion by Combing Open-Loop and Closed-Loop Approaches," U.S. Provisional Application No. 61/988,296 filed on May 4, 2014, entitled "Simplified Beamformer and Noise Canceller for Speech Enhancement," U.S. Provisional Application No. 61/988,297 filed on May 4, 2014, entitled "Single MIC Detection in Beam-former and Noise Canceller for Speech Enhancement," U.S. Provisional Application No. 61/988,299 filed on May 4, 2014, entitled "Noise Energy Controlling In Noise Reduction System With Two Microphones," which application is hereby incorporated herein by reference.

TECHNICAL FIELD

The present invention is generally in the field of Noise Reduction/Speech Enhancement. In particular, the present invention is used to improve Microphone Array Beamformer for background noise cancellation or interference signal cancellation.

BACKGROUND

Beamforming is a technique which extracts the desired signal contaminated by interference based on directivity, i.e., spatial signal selectivity. This extraction is performed by processing the signals obtained by multiple sensors such as microphones located at different positions in the space. The principle of beamforming has been known for a long time. Because of the vast amount of necessary signal processing, most research and development effort has been focused on geological investigations and sonar, which can afford a high cost. With the advent of LSI technology, the required amount of signal processing has become relatively small. As a result, a variety of research projects where acoustic beamforming is applied to consumer-oriented applications such as cellular phone speech enhancement, have been carried out. Microphone array could contain multiple microphones; for the simplicity, two microphones array system is widely used.

Applications of beamforming include microphone arrays for speech enhancement. The goal of speech enhancement is to remove undesirable signals such as noise and reverberation. Amount research areas in the field of speech enhancement are teleconferencing, hands-free telephones, hearing aids, speech recognition, intelligibility improvement, and acoustic measurement.

Beamforming can be considered as multi-dimensional signal processing in space and time. Ideal conditions assumed in most theoretical discussions are not always maintained. The target DOA (direction of arrival), which is assumed to be stable, does change with the movement of the speaker. The sensor gains, which are assumed uniform, exhibit significant distribution. As a result, the performance obtained by beamforming may not be as good as expected. Steering vector errors are inevitable because the propagation model does not always reflect the non-stationary physical environment. The steering vector is sensitive to errors in the microphone positions, those in the microphone characteristics, and those in the assumed target DOA (which is also known as the look direction). For teleconferencing and hands-free communication, the error in the assumed target DOA is the dominant factor. Therefore, robustness against steering-vector errors caused by these array imperfections are become more and more important.

A beamformer which adaptively forms its directivity pattern is called an adaptive beamformer. It simultaneously performs beam steering and null steering. In most traditional acoustic beamformers, however, only null steering is performed with an assumption that the target DOA is known a priori. Due to adaptive processing, deep nulls can be developed. Adaptive beamformers naturally exhibit higher interference suppression capability than its fixed counterpart which may be called fixed beamformer.

The traditional adaptive beamformer/noise cancellation suffers from target speech signal cancellation due to steering vector errors, which is caused by an undesirable phase difference between two microphones input signals for the target. This is specially true when the target source or the microphone array is moving in space. Even if the phase between two microphones input signals is aligned, the output target signal from a fixed beamformer could still possibly have lower SNR (target signal to noise ratio) than the best one of the microphone array component signals; this means that one of the microphones could possibly receive higher SNR than the output target signal from a fixed beamformer. A phase error leads to target signal leakage, which results in target signal cancellation at the output. Adaptive filter technology is a widely used to adaptively and precisely align the target signals from different microphones; correctly controlling a step size of the adaptive filter is the key to have a robust performance.

SUMMARY

In accordance with an embodiment of the present invention, a noise reduction method for speech processing includes estimating a noise/interference component signal by subtracting voice component signal from a first microphone input signal wherein the voice component signal is evaluated as a first replica signal produced by passing a second microphone input signal through a first adaptive filter; a stepsize is estimated to control adaptive update of the first adaptive filter, wherein the stepsize is evaluated by combing an open-loop approach and a closed-loop approach, the open-loop approach comprising voice/noise/interference classification and SNR estimation in voice area, and the closed-loop approach comprising calculating a normalized correlation between the first replica signal and the first microphone input signal. A noise/interference reduced signal is outputted by subtracting a second replica signal from a target signal which is the first microphone input signal or the second microphone input signal, wherein the second replica signal is produced by passing the estimated noise/interference component signal through a second adaptive filter.

In an alternative embodiment, a speech processing apparatus comprises a processor, and a computer readable storage medium storing programming for execution by the processor. The programming include instructions to estimate a noise/interference component signal by subtracting voice component signal from a first microphone input signal wherein the voice component signal is evaluated as a first replica signal produced by passing a second microphone input signal through a first adaptive filter; a stepsize is estimated to control adaptive update of the first adaptive filter, wherein the stepsize is evaluated by combing an open-loop approach and a closed-loop approach, the open-loop approach comprising voice/noise/interference classification and SNR estimation in voice area, and the closed-loop approach comprising calculating a normalized correlation between the first replica signal and the first microphone input signal. A noise/interference reduced signal is outputted by subtracting a second replica signal from a target signal which is the first microphone input signal or the second microphone input signal, wherein the second replica signal is produced by passing the estimated noise/interference component signal through a second adaptive filter.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF ILLUSTRATIVE EMBODIMENTS

Figure 1:
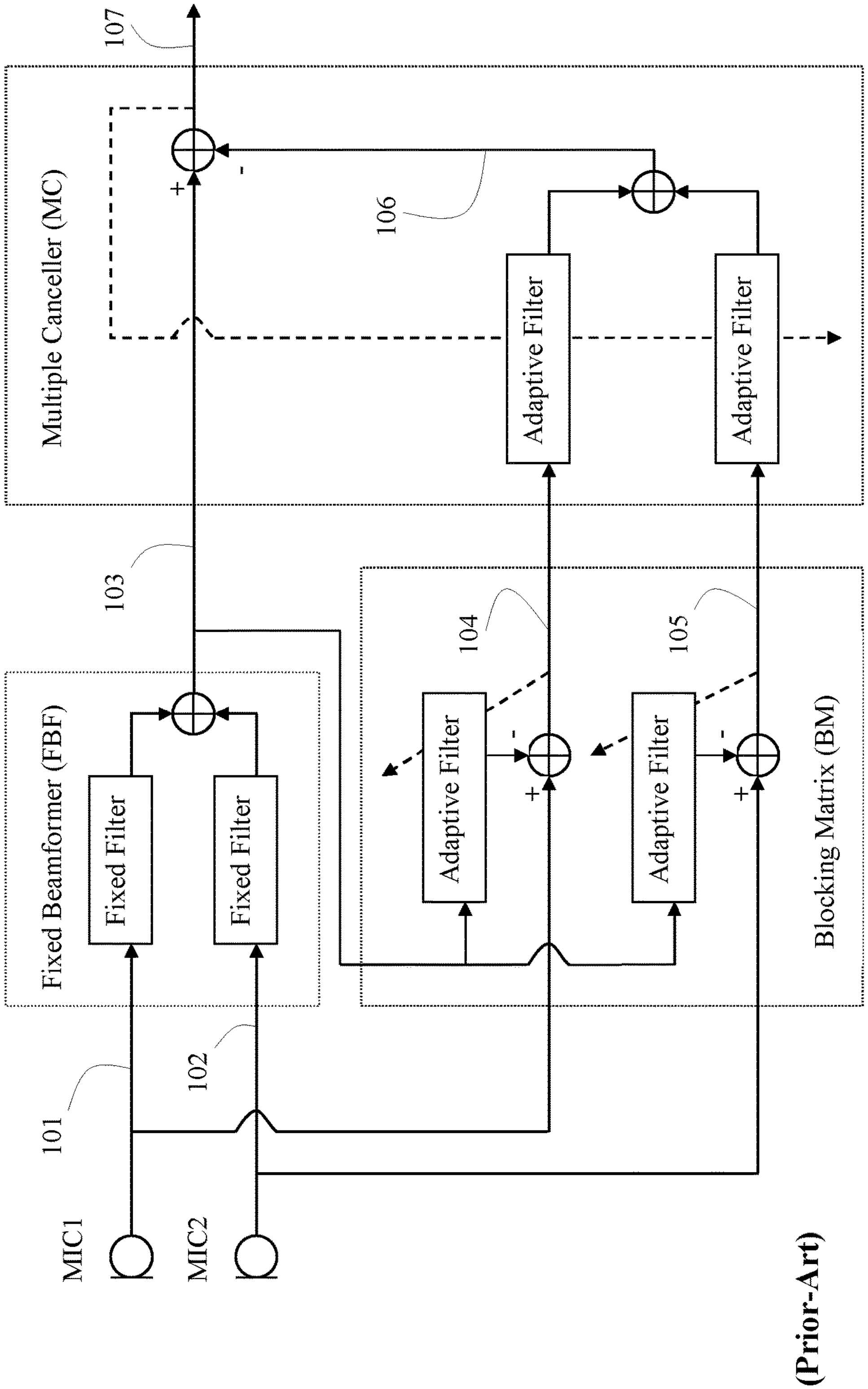
FIG. 1 illustrates a structure of a widely known adaptive beamformer among various adaptive beamformers. For the simplicity, only two microphones are shown.

FIG. 1 depicts a structure of a widely known adaptive beamformer among various adaptive beamformers. Microphone array could contain multiple microphones; for the simplicity, FIG. 1 only shows two microphones. FIG. 1 comprises a fixed beamformer (FBF), a multiple input canceller (MC), and blocking matrix (BM). The FBF is designed to form a beam in the look direction so that the target signal is passed and all other signals are attenuated. On the contrary, the BM forms a null in the look direction so that the target signal is suppressed and all other signals are passed through. The inputs 101 and 102 of FBF are signals coming from MICs. 103 is the output target signal of FBF. 101, 102 and 103 are also used as inputs of BM. The MC is composed of multiple adaptive filters each of which is driven by a BM output. The BM outputs 104 and 105 suppose to contain all the signal components except that in the look direction or that of the target signal. Based on these signals, the adaptive filters in MC generate replicas 106 of components correlated with the interferences. All the replicas are subtracted from a delayed output signal of the fixed beamformer which contains an enhanced target signal component. In the subtracter output 107, the target signal is enhanced and undesirable signals such as ambient noise and interferences are suppressed.

Figure 2:
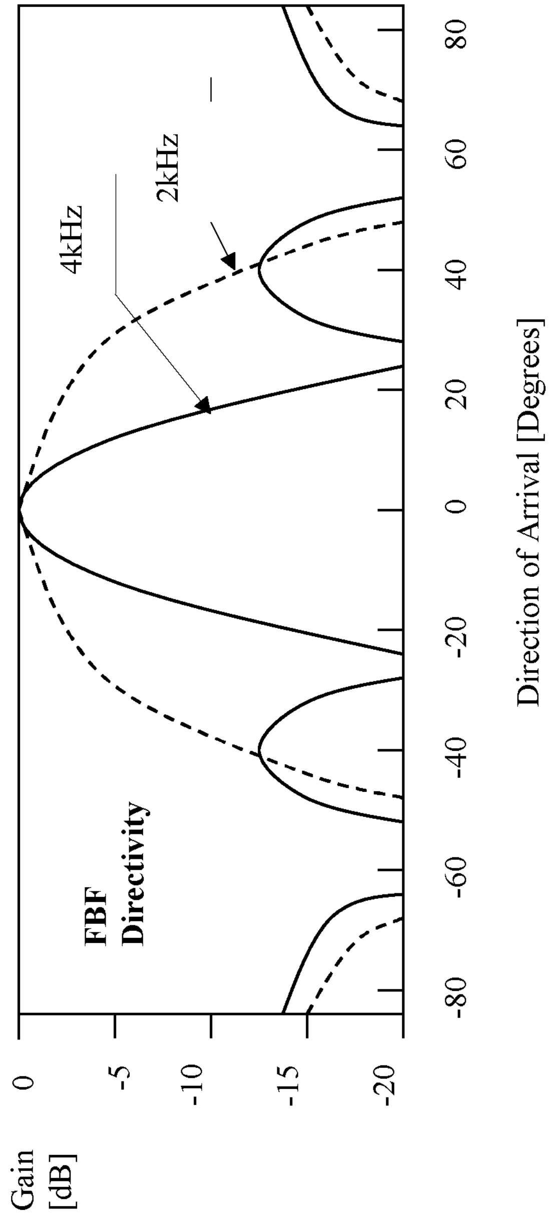
Figure 2 (Prior Art)
FIG. 2 illustrates an example of directivity of a fixed beamformer which outputs a target signal.

FIG. 2. shows an example of directivity of the FBF wherein the highest gain is shown in the looking direction.

Figure 3:
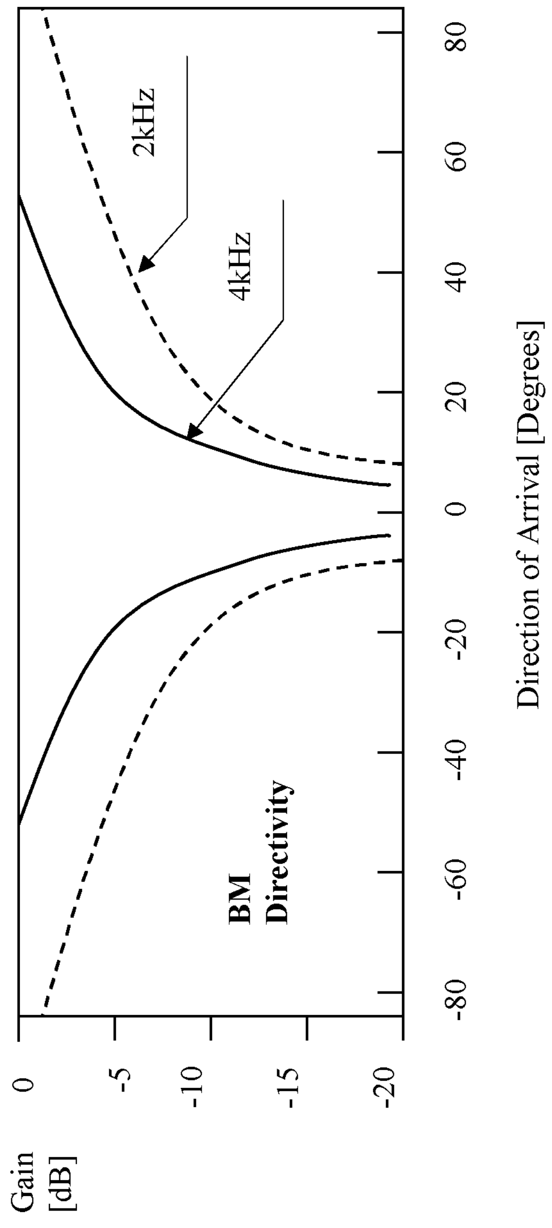
Figure 3 (Prior Art)
FIG. 3 illustrates an example of directivity of a block matrix which outputs reference noise/interference signals.

FIG. 3. shows an example of directivity of the BM wherein the lowest gain is shown in the looking direction.

In real applications, the looking direction of the microphones array does not always or exactly faces the coming direction of the target signal source. For example, in teleconferencing and hands-free communication, there are several speakers located at different positions while the microphones array is fixed and not adaptively moved to face the speaker. Another special example is stereo application in which the two signals from two microphones can not be mixed to form one output signal otherwise the stereo characteristic is lost. The above traditional adaptive beamformer/noise cancellation suffers from target speech signal cancellation due to steering vector errors, which is caused by an undesirable phase difference between two microphones input signals for the target. This is specially true when the target source or the microphone array is randomly moving in space. Even if the phase between two microphones input signals is aligned, the output target signal from the FBF could still possibly have lower SNR (target signal to noise ratio) than the best one of the microphone array component signals; this means that one of the microphones could possibly receive higher SNR than the mixed output target signal from the FBF. A phase error leads to target signal leakage into the BM output signal. As a result, blocking of the target becomes incomplete in the BM output signal, which results in target signal cancellation at the MC output. Steering vector errors are inevitable because the propagation model does not always reflect the non-stationary physical environment. The steering vector is sensitive to errors in the microphone positions, those in the microphone characteristics, and those in the assumed target DOA (which is also known as the look direction). For teleconferencing and hands-free communication, the error in the assumed target DOA is the dominant factor.

Figure 4:
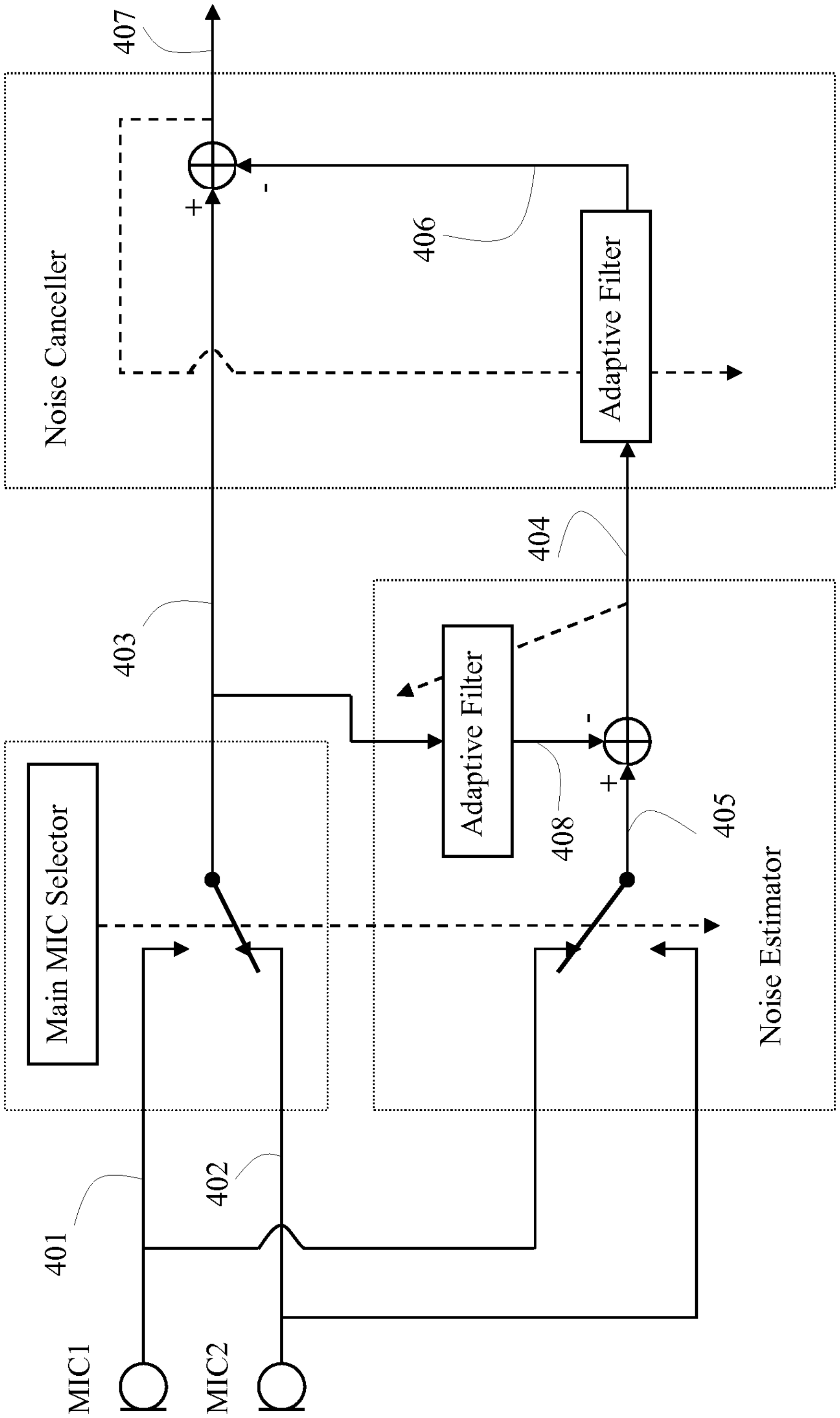
FIG. 4 illustrates a simplified beamformer/interference canceller for mono output system.

FIG. 4 proposed a simplified beamformer and noise canceller. Instead of using two fixed filters and four adaptive filters with FIG. 1 system, only two adaptive filters are used in FIG. 4 system. 401 and 402 are two input signals respectively from MIC1 (microphone 1) and MIC2 (microphone 2). The speech target signal 403 is selected as one of the two input signals from MIC1 and MIC2. The selected MIC is named as Main MIC. In mono output application, the Main MIC is adaptively selected from the two microphones, the detailed selection algorithm is out of the scope of this specification. In stereo output application, MIC1 is always selected as the Main MIC for one channel output and MIC2 is always selected as the Main MIC for another channel output. Unlike the speech target signal 103 in FIG. 1, which possibly has worse quality than the best one of the two input signals 101 and 102 from MIC1 and MIC2, the Main MIC Selector in FIG. 4 guarantees that the quality of the speech target signal 403 is not worse than the best one of the two input signals 401 and 402 from MIC1 and MIC2. For example, in mono output application, if the Main MIC Selector selects MIC2 as the main MIC, the Noise Estimator could take MIC1 or MIC2 signal as its input 405; in the case of taking MIC1 signal as its input 405, the MIC2 signal 403 passes through an adaptive filter to produce a replica signal 408 which tries to match the voice portion in the MIC1 signal 405; the replica signal 408 is used as a reference signal to cancel the voice portion in the MIC1 signal 405 in the Noise Estimator in order to obtain the noise/interference estimation signal 404. This noise/interference estimation signal 404 inputs to the Noise Canceller which works with an adaptive filter to produce a noise/interference replica 406 matching the noise/interference portion in the target signal 403. A noise/interference reduced speech signal 407 is obtained by subtracting the noise/interference replica signal 406 from the target signal 403. Comparing the traditional FIG. 1 system with the FIG. 4 system, not only the complexity of the FIG. 4 system is significantly reduced; but also the over-all performance of the FIG. 4 system becomes more robust.

Figure 5:
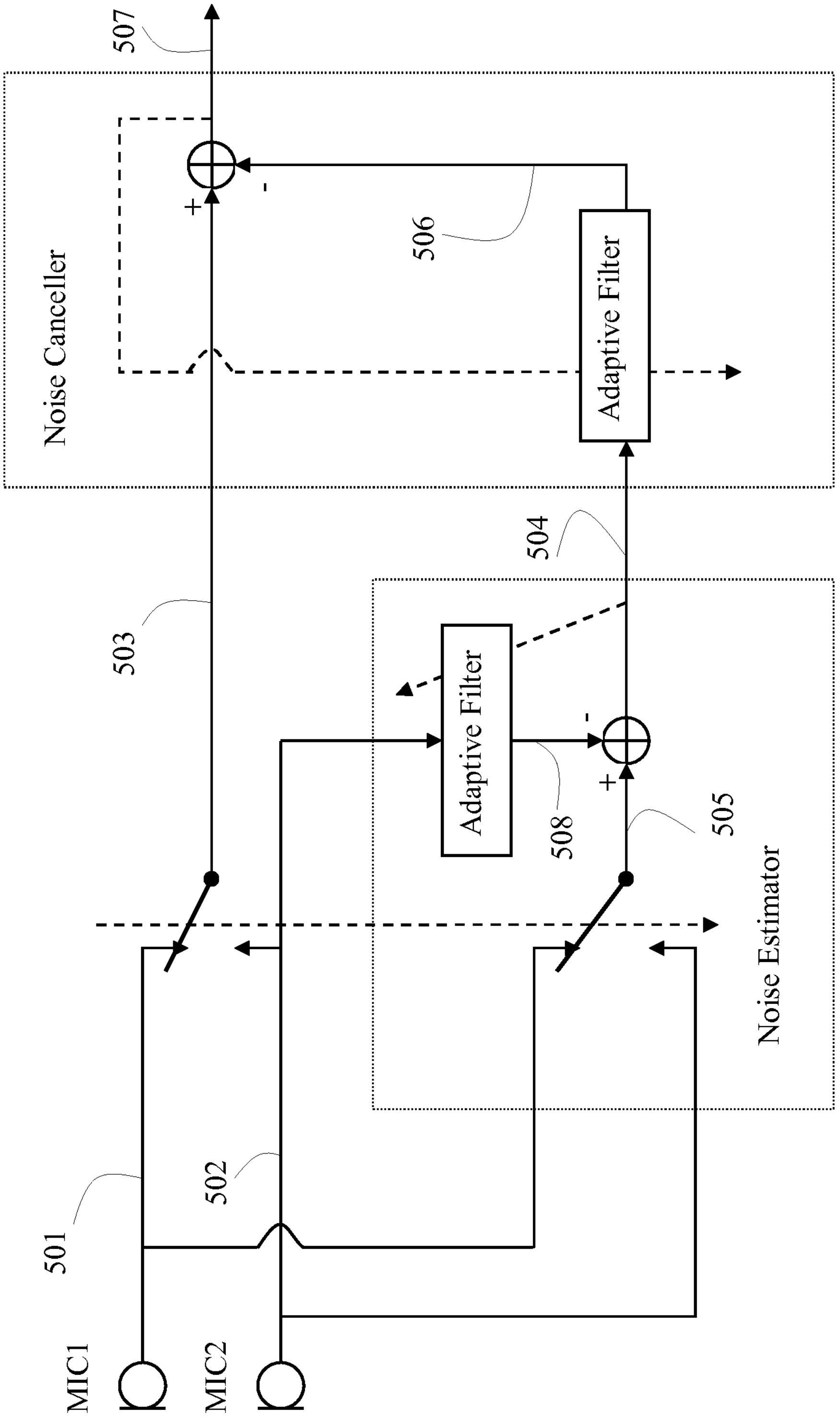
FIG. 5 illustrates a simplified beamformer/interference canceller for stereo output system.

FIG. 5 proposed a simplified beamformer and noise canceller for stereo output. In stereo application, one channel output should keep the difference from another channel output; in this case, we can not choose one channel output that has better quality than another channel; however, we can use another channel to reduce/cancel the noise/interference in the current channel; it is still based on the beamforming principle. FIG. 5 shows the noise/interference cancellation system for the channel signal from MIC1; the noise/interference cancellation system for the channel signal from MIC2 can be designed in a similar or symmetric way. As the system in FIG. 4, only two adaptive filters are used in FIG. 5 system instead of using two fixed filters and four adaptive filters with FIG. 1 system. 501 and 502 are two input signals respectively from MIC1 (microphone 1) and MIC2 (microphone 2). The speech target signal 503 is simply selected from MIC1. In stereo output application, MIC1 is always selected as the Main MIC for one channel output and MIC2 is always selected as the Main MIC for another channel output. For example, in stereo output application, if MIC1 is the main MIC, the Noise Estimator could take MIC1 signal as its input 505; the MIC2 signal 502 passes through an adaptive filter to produce a replica signal 508 which tries to match the voice portion in the MIC1 signal 505; the replica signal 508 is used as a reference signal to cancel the voice portion in the MIC1 signal 505 in the Noise Estimator in order to obtain the noise/interference estimation signal 504. This noise/interference estimation signal 504 inputs to the Noise Canceller which works with an adaptive filter to produce a noise/interference replica 506 matching the noise/interference portion in the target signal 503. A noise/interference reduced speech signal 507 is obtained by subtracting the noise/interference replica signal 506 from the target signal 503.

In the FIG. 4 system or FIG. 5 system, the Noise Estimator or BM is an important diagram block. The performance of the Noise Canceller highly depends on the quality of the estimated noise 404 or 504. This is specially true for unstable noise. In order to have a nice noise estimation in voice area, the voice component (but not the noise component) in the input signal 405 or 505 needs to be cancelled; this is achieved by producing a replica signal 408 or 508 matching the voice component in the input signal 405 or 505; in general, the smaller is the difference between the voice component in the input signal 405/505 and the replica signal 408/508 from the adaptive filter, the better quality has the estimated noise 404 or 504. The adaptive filter is an FIR filter, the impulsive response of which is theoretically adapted in such way that the difference between the voice component in 405/505 and the replica signal 408/508 is minimized. In realty, the exact voice component in 405 or 505 is not known; instead, the adaptation algorithm of the adaptive filter impulsive response is conducted by minimizing the difference between the 405/505 signal and the 408/508 signal in voice area; we can imagine that emphasizing the filter adaptation in high SNR voice area may achieve better quality than low SNR voice area. The goal of the control of the adaptive filter is to minimize the leakage of voice component into the noise signal 404 or 504.

The impulsive response of the adaptive filter in the Noise Estimator can be expressed as, $$h(n)=[h_0(n),h_1(n),h_2(n), \ldots ,h_{N-1}(n)] \tag{1}$$

wherein N is the filter order, the subscript $i\in\{0, 1, 2, \ldots, N-1\}$ addresses the ith coefficient of the impulsive response of the adaptive filter at the time index n. In general, a normalized least mean square algorithm leads to the impulsive response h(n) updated at each time index n in voice area:

$$h(n+1)=h(n)+\mu\cdot\Delta h(n) \tag{2}$$

wherein $\Delta h(n)$ is the maximum update portion and $\mu$, $0\le\mu\le1$, is the stepsize which controls the update amount at each time index. Suppose the signal 403 in FIG. 4 or 502 in FIG. 5 is noted as $x_2(n)$, the signal 405 or 505 is noted as $x_1(n)$, the replica signal 408 or 508 is noted as d(n), and the difference signal 404 or 504 is noted as e(n). The maximum update portion can be expressed as, $$\Delta h(n) = \frac{x_2(n)\cdot e(n)}{\|x_2(n)\|^2} \tag{3}$$

wherein $x_2(n)$ is a vector of the signal 403 or 502 $x_2(n)$ with a length N and $$e(n)=x_1(n)-d(n) \tag{4}$$

$$d(n)=h^T(n)\cdot x_2(n) \tag{5}$$

The key factor for the performance of the adaptive filter is the determination of the stepsize $\mu$, $0\le\mu\le1$. As the goal is to cancel voice component, in noise area the stepsize $\mu$ is set to zero and the adaptive filter is not updated. In voice area, an appropriate stepsize $\mu$ value should be set; usually, the stepsize $\mu$ should be high in high SNR area and low in low SNR area. Too low stepsize $\mu$ could cause the convergence speed of the adaptive filter is too slow so that some voice portion may not be cancelled; too high stepsize $\mu$ could possibly cause unstable adaptive filter or cancelling needed noise portion.

Figure 6:
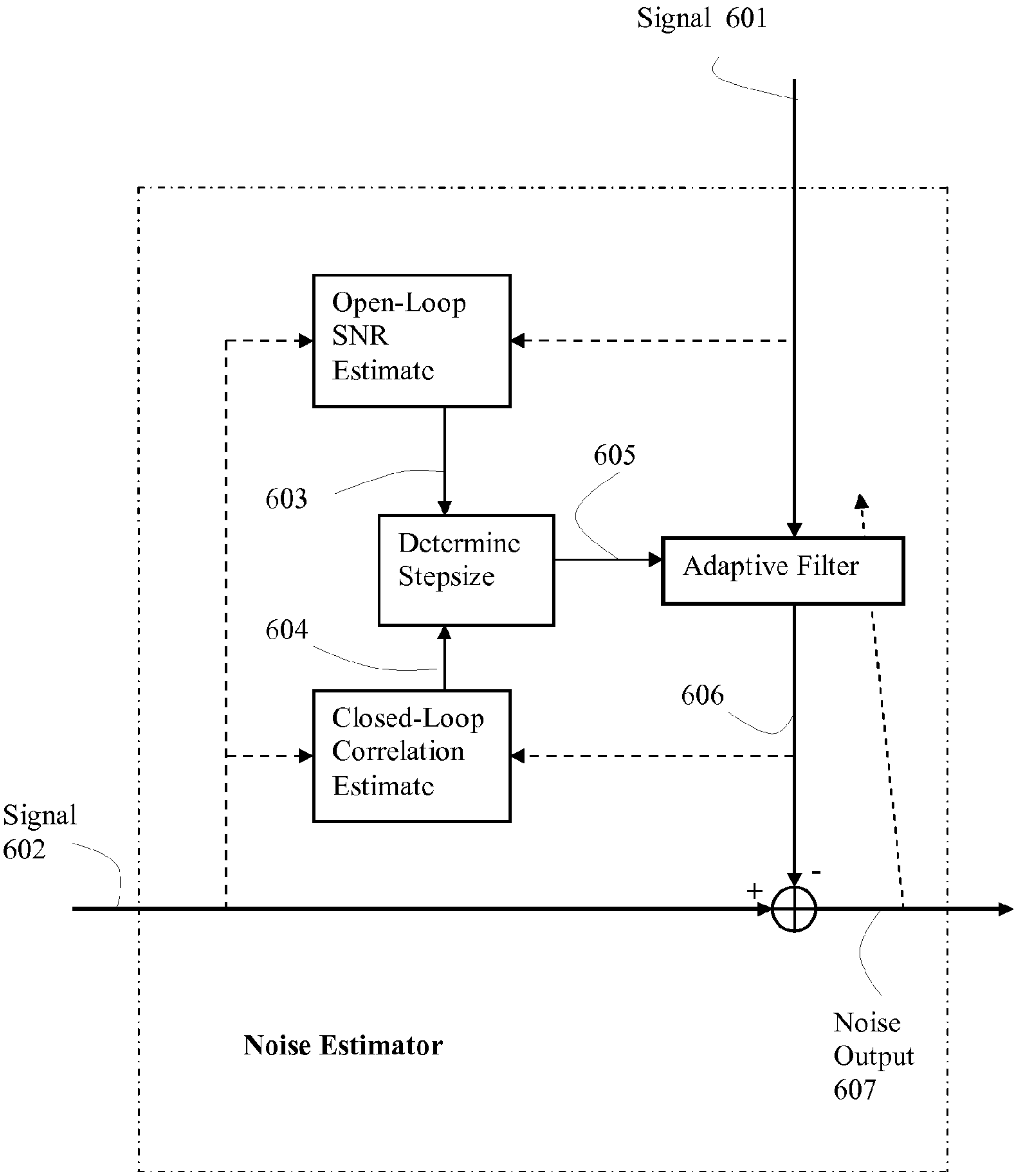
FIG. 6 illustrates a general principle of step size determination used for adaptive filter in noise/interference estimator.

FIG. 6 proposed a robust determination approach of the stepsize, which combines an open-loop approach and a closed-loop approach. The open-loop approach uses available information to determine the stepsize before the adaptive filter is performed for current frame without counting the filtering result; the closed-loop approach determines the stepsize by considering possible filtering result after the adaptive filter is performed. As the stepsize needs to be determined before the adaptive filtering is performed for the current frame, the filter coefficients updated in the last frame may be used to estimate possible current result in the closed-loop approach; this is reasonable as the difference between the current filter coefficients and the last filter coefficients is usually very small. The advantage of the open-loop approach is that it is relatively simple and still works when the difference between the current frame and the last frame is large; but the open-loop approach strongly relies on correct estimation of some parameters such as SNR and/or a decision between voice and interference; sometimes, the noise is an interference signal which is unstable and similar to voice signal; a correct estimation of SNR is difficult especially when the noise is not stable. The advantage of the closed-loop approach is that it is reliable during most time even if the noise is unstable; but the closed-loop approach may fail when the difference between the current filter coefficients and the last filter coefficients should be large. An appropriate combination of the open-loop approach and the closed-loop approach can result in a robust algorithm of determining the stepsize. FIG. 6 shows a basic principle of combining the open-loop approach and the closed-loop approach. Suppose the main MIC is MIC2 for mono output system; the MIC1 signal 602 is usually noisier than the MIC2 signal 601 in this case. For stereo output case, 602 could be noisier than 601 or 601 could be noisier than 602. An initial stepsize 603 is first estimated based on an open-loop SNR (in voice area) parameter obtained by analyzing the MIC1 signal 602 and the MIC2 signal 601. Closed-loop correlation parameters 604 are employed to correct and limit the initial stepsize value 603. An efficient closed-loop parameter may be a normalized correlation between a current 602 signal vector and an estimated replica signal vector 606 which is obtained by passing a current 601 signal vector through the adaptive filter updated in a last frame. A determined stepsize parameter 605 for a current frame is used to control the updating of the current adaptive filter. A current replica signal 606 is obtained by passing the current 601 signal through the currently updated adaptive filter. Finally, the noise/interference estimation 607 is calculated by subtracting the replica signal 606 from the 602 signal.

Figure 7:
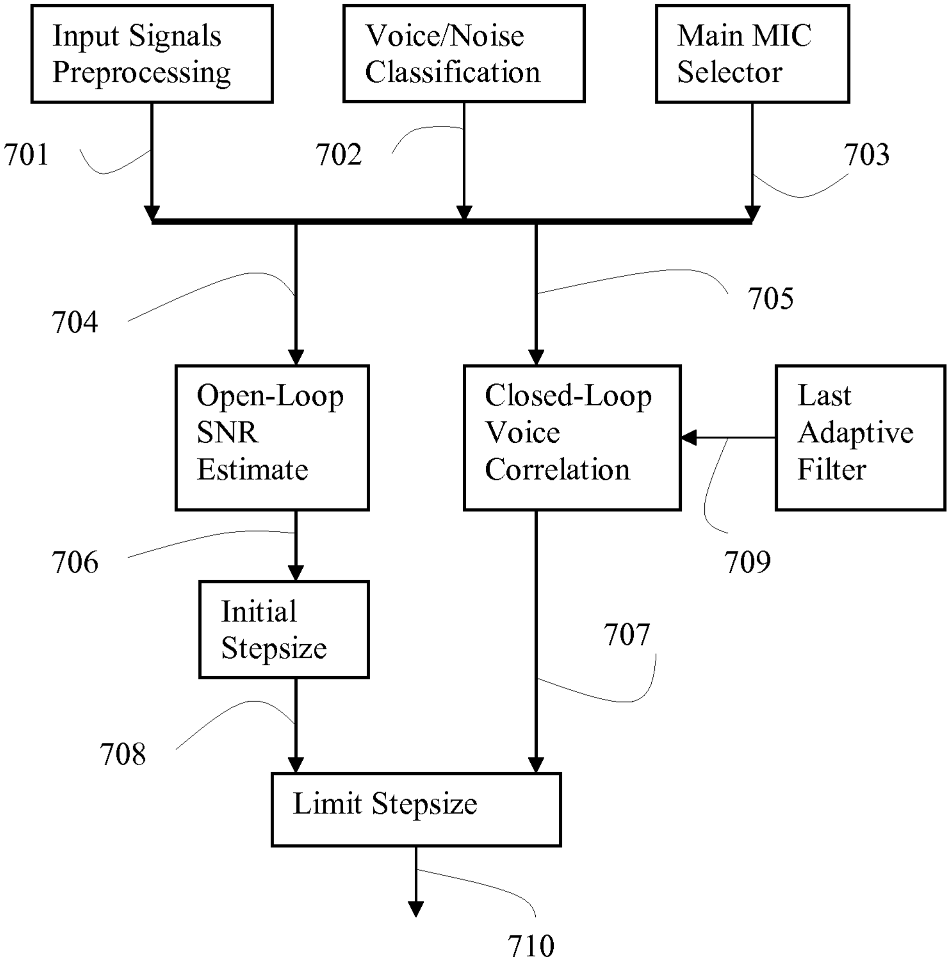
FIG. 7 illustrates a procedure of step size determination used for adaptive filter in noise/interference estimator.

FIG. 7 shows a more detailed procedure to determining the stepsize by combing the open-loop approach and the closed-loop approach. Input signals from MICs are first preprocessed to obtain the preprocessed signals 701. The preprocessed signals are analyzed to perform voice/noise/interference classifications such as VAD (Voice Activity Detection). The main MIC selection is performed based on the classification information 702 and the preprocessed signals 701 to set the main MIC flag 703 in mono output application. In stereo output application, the main MIC is left MIC for left channel output; the main MIC is right MIC for right channel output. Selectively combined information 704 is used to have an open-loop SNR estimate. Another selectively combined information 705 is used to evaluate a closed-loop correlation between one noisy input signal and a replica signal obtained by passing another input signal through a last adaptive filter 709. The open-loop SNR parameter 706 is used to set up an initial stepsize 708. The closed-loop voice correlation parameter 707 is evaluated to correct and limit the initial stepsize 708 and determine the final stepsize 710 for updating the current adaptive filter.

Figure 8:
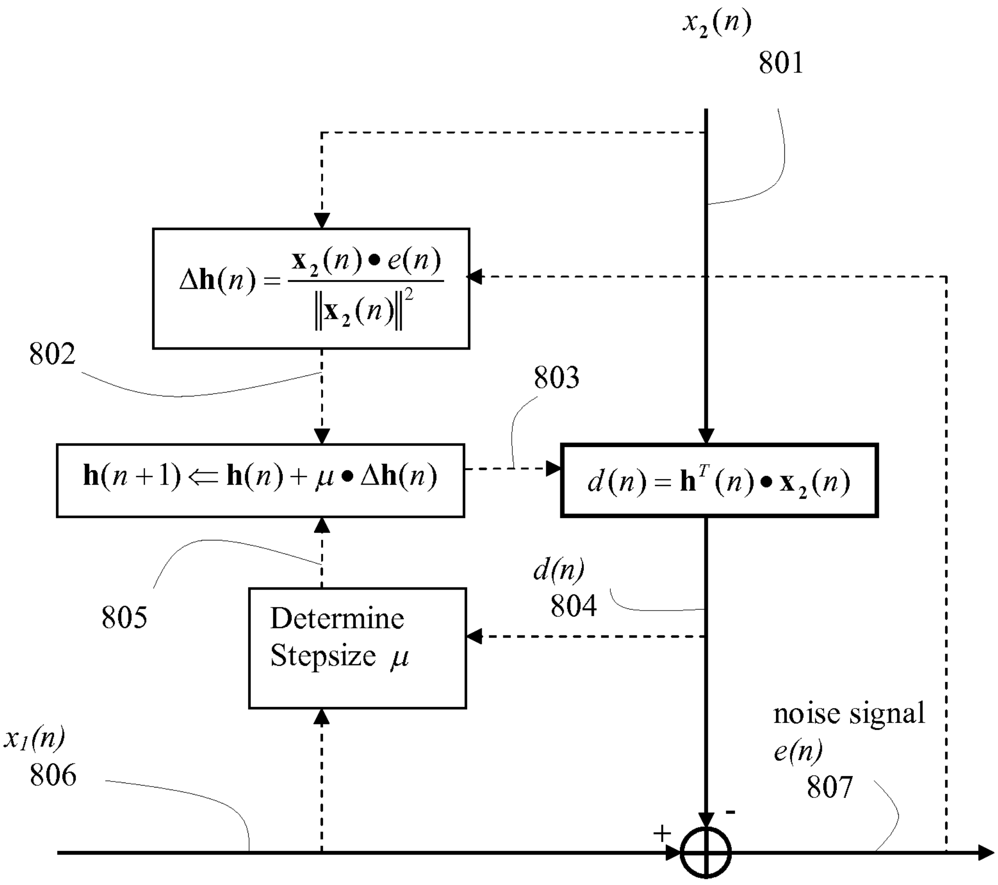
FIG. 8 illustrates a structure of adaptive filter with step size control.

FIG. 8 shows a mathematical procedure of the adaptive filter. The maximum stepsize vector 802 is the error signal e(n) 807 normalized by the reference input signal $x_2(n)$ 801. After determining the stepsize 805, an adaptive filter coefficient vector 803 is updated. A replica signal 804 is produced by passing the signal 801 through the updated adaptive filter. An estimated noise signal 807 is finally obtained by subtracting the replica signal 804 from the signal 806.

The following is a detailed example for the stepsize determination. Some parameters are first defined as:

SNR_L: SNR estimate (in dB) of a low frequency band signal of the signal 806;

SNR_F: SNR estimate (in dB) of a full frequency band signal of the signal 806;

SNR0=Maximum {SNR_L, SNR_F};

SNR1: Modified SNR;

diff_SNR: difference between the current full band SNR and the smoothed full band SNR;

VoiceFlag=1 means voiced area, otherwise noise area;

speech_flag=1 means extended voiced area, otherwise noise area;

μ: stepsize for updating the adaptive filter impulsive response;

μ_sm: smoothed stepsize for updating the adaptive filter impulsive response;

Corr_Tx1Tx2: the normalized correlation between the signal 806 and the replica signal 804;

Corr_Tx1Tx2_sm: the short-term smoothed Corr_Tx1Tx2;

Corr_Tx1Tx2_sm2: the smoothed normalized correlation between the signal 806 and the replica signal 804 in noise area;

CloseVcorr_sm: the long-term smoothed Corr_Tx1Tx2;

CloseVcorr_sm2: the long-term smoothed Corr_Tx1Tx2_sm2;

update_cnt: the stepsize update counting;

NoiseFlag=1 means noise area; otherwise, speech area.

For the clarity, some names commonly used in the technical domain are expressed as follows in a mathematical way. "energy" means an energy calculated on a frame of digital signal s(n), n is time index on the frame:

$$\text{Energy} = \sum_n [s(n)]^2 \tag{6}$$

"energy" can be expressed in dB domain:

$$\text{Energy\_dB} = 10 \cdot \log\left(\sum_n [s(n)]^2\right) \tag{7}$$

"SNR" means an energy ratio between signal energy and noise energy, which can be in linear domain or dB domain; "normalized correlation" between signal $s_1(n)$ and signal $s_2(n)$ can be defined as:

$$\text{Corr} = \frac{\sum_n s_1(n) \cdot s_2(n)}{\sqrt{\left(\sum_n [s_1(n)]^2\right) \cdot \left(\sum_n [s_1(n)]^2\right)}} \tag{8}$$

or it can be defined as:

$$\text{Corr} = \frac{\left[\sum_n s_1(n) \cdot s_2(n)\right]^2}{\left(\sum_n [s_1(n)]^2\right) \cdot \left(\sum_n [s_1(n)]^2\right)} \tag{9}$$

In (9), assumme $$\sum_n s_1(n) \cdot s_2(n) > 0;$$

otherwise set Corr=0. The following is the detailed example for the stepsize determination:

```
Initial Stepsize : μ = 0 ;
If (strong voice signal is detected) {
            μ = 0.5 ;
}
Else {
            SNR1 = MIN(MAX( (SNR0-6)/10, 0), 1);
            μ = SNR1² · VoiceFlag · 0.6 ;
            μ = MIN(μ, 0.5) ;
}
DiffCorr2 = Corr_Tx1Tx2 − Corr_Tx1Tx2_sm2;
DiffCorr3 = CloseVcorr_sm − CloseVcorr_sm2;
sqr_corr_min = MIN(Corr_Tx1Tx2, Corr_Tx1Tx2_sm);
If (Corr_Tx1Tx2<0.1 AND DiffCorr2<0.1 AND DiffCorr3<0.1
     AND update_cnt>100)
{
            μ ⇐ μ · 0.75 ;
}
If ( (speech_flag OR update_cnt>64) AND SNR0>5 AND
          diff_SNR>−5 AND (sqr_corr_min >0.65 OR
        (sqr_corr_min>0.6 AND Corr_Tx1Tx2>0.8) OR
        Corr_Tx1Tx2>0.9) )
{
            Limit = (Corr_Tx1Tx2−0.5) 0.8/0.5;
            μ = MAX{μ , Limit} ;
            VoiceFlag=1; //flag modification
}
If (DiffCorr2>0.4 AND ( (sqr_corr_min>0.4) OR
     (CloseVcorr_sm>0.2 AND DiffCorr3>0) ) AND
     SNR0>5 AND diff_SNR>−5)
{
            LIMIT=MIN{ (DiffCorr2−0.2f)/0.8, 0.6} ;
            μ = MAX(μ, Limit} ;
}
If (DiffCorr2>0.2 AND DiffCorr3>0.1 AND Corr_Tx1Tx2>0.5 AND
      SNR0>5 AND diff_SNR>−5)
{
            Limit= MIN{ (DiffCorr2−0.1f)/0.9, 0.6};
            μ = MAX{μ , Limit} ;
}
If ( (Corr_Tx1Tx2<0.01 AND DiffCorr2<0.1 AND DiffCorr3<0.05
            AND update_cnt>100) OR NoiseFlag)
{
            μ = MIN{μ, 0.05} ;
}
If (Click Interference sound exists)
{
            μ = 0 ;
}
If (update_cnt<200)
{
            μ = MIN{μ · 1.5, 0.8} ;
}
If ( μ, > μ_sm OR Click exists)
{
            μ_sm = μ ;
}
Else {
              μ_sm= 0.25μ _ sm⁝+ 0.75μ ;
}
If ( μ > 0.01)
{
            update_cnt <= update_cnt + 1 ;
}
```

Figure 9:
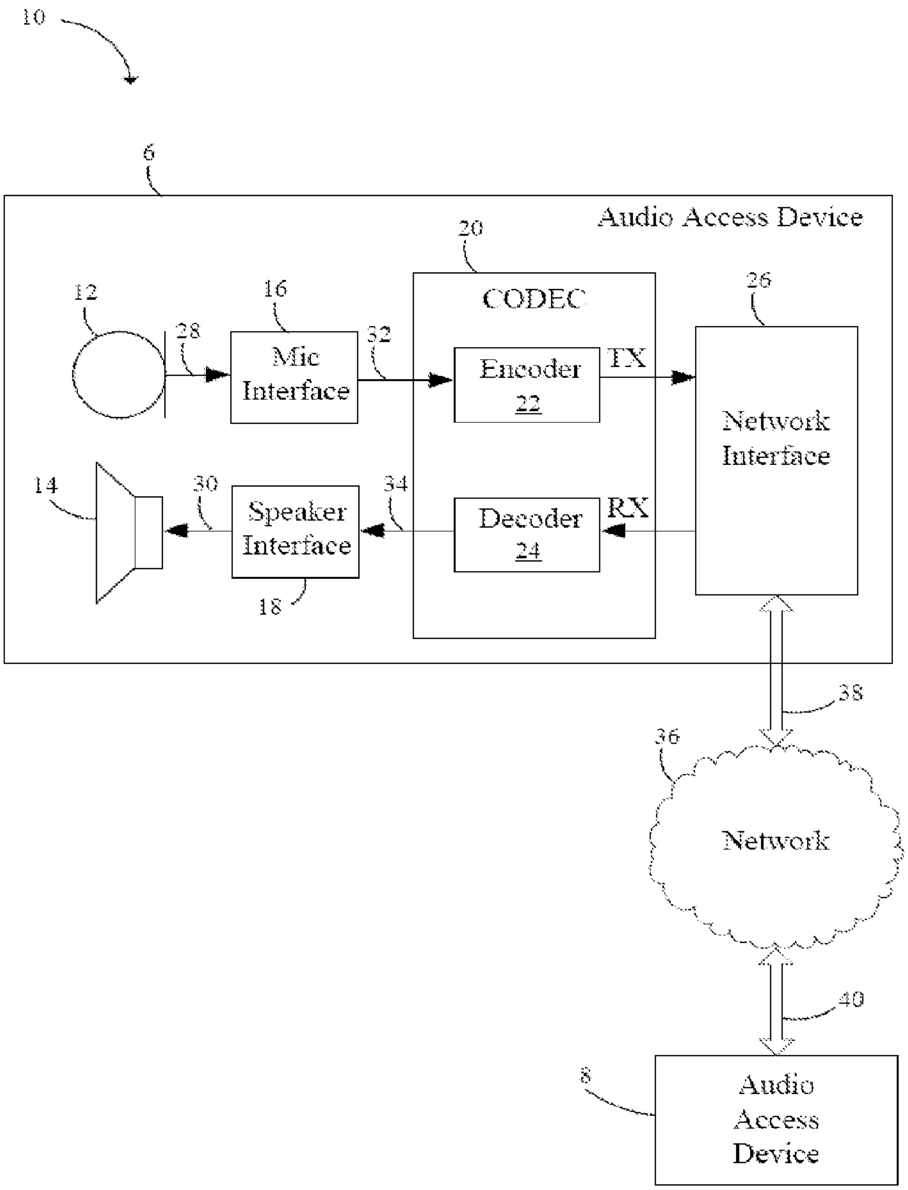
FIG. 9 illustrates a communication system according to an embodiment of the present invention.

FIG. 9 illustrates a communication system 10 according to an embodiment of the present invention.

Communication system 10 has audio access devices 7 and 8 coupled to a network 36 via communication links 38 and 40. In one embodiment, audio access device 7 and 8 are voice over internet protocol (VOIP) devices and network 36 is a wide area network (WAN), public switched telephone network (PTSN) and/or the internet. In another embodiment, communication links 38 and 40 are wireline and/or wireless broadband connections. In an alternative embodiment, audio access devices 7 and 8 are cellular or mobile telephones, links 38 and 40 are wireless mobile telephone channels and network 36 represents a mobile telephone network.

The audio access device 7 uses a microphone 12 to convert sound, such as music or a person's voice into an analog audio input signal 28. A microphone interface 16 converts the analog audio input signal 28 into a digital audio signal 33 for input into an encoder 22 of a CODEC 20. The encoder 22 can include a speech enhancement block which reduces noise/interferences in the input signal from the microphone(s). The encoder 22 produces encoded audio signal TX for transmission to a network 26 via a network interface 26 according to embodiments of the present invention. A decoder 24 within the CODEC 20 receives encoded audio signal RX from the network 36 via network interface 26, and converts encoded audio signal RX into a digital audio signal 34. The speaker interface 18 converts the digital audio signal 34 into the audio signal 30 suitable for driving the loudspeaker 14.

In embodiments of the present invention, where audio access device 7 is a VOIP device, some or all of the components within audio access device 7 are implemented within a handset. In some embodiments, however, microphone 12 and loudspeaker 14 are separate units, and microphone interface 16, speaker interface 18, CODEC 20 and network interface 26 are implemented within a personal computer. CODEC 20 can be implemented in either software running on a computer or a dedicated processor, or by dedicated hardware, for example, on an application specific integrated circuit (ASIC). Microphone interface 16 is implemented by an analog-to-digital (A/D) converter, as well as other interface circuitry located within the handset and/or within the computer. Likewise, speaker interface 18 is implemented by a digital-to-analog converter and other interface circuitry located within the handset and/or within the computer. In further embodiments, audio access device 7 can be implemented and partitioned in other ways known in the art.

In embodiments of the present invention where audio access device 7 is a cellular or mobile telephone, the elements within audio access device 7 are implemented within a cellular handset. CODEC 20 is implemented by software running on a processor within the handset or by dedicated hardware. In further embodiments of the present invention, audio access device may be implemented in other devices such as peer-to-peer wireline and wireless digital communication systems, such as intercoms, and radio handsets. In applications such as consumer audio devices, audio access device may contain a CODEC with only encoder 22 or decoder 24, for example, in a digital microphone system or music playback device. In other embodiments of the present invention, CODEC 20 can be used without microphone 12 and speaker 14, for example, in cellular base stations that access the PTSN.

The speech processing for reducing noise/interference described in various embodiments of the present invention may be implemented in the encoder 22 or the decoder 24, for example. The speech processing for reducing noise/interference may be implemented in hardware or software in various embodiments. For example, the encoder 22 or the decoder 24 may be part of a digital signal processing (DSP) chip.

Figure 10:
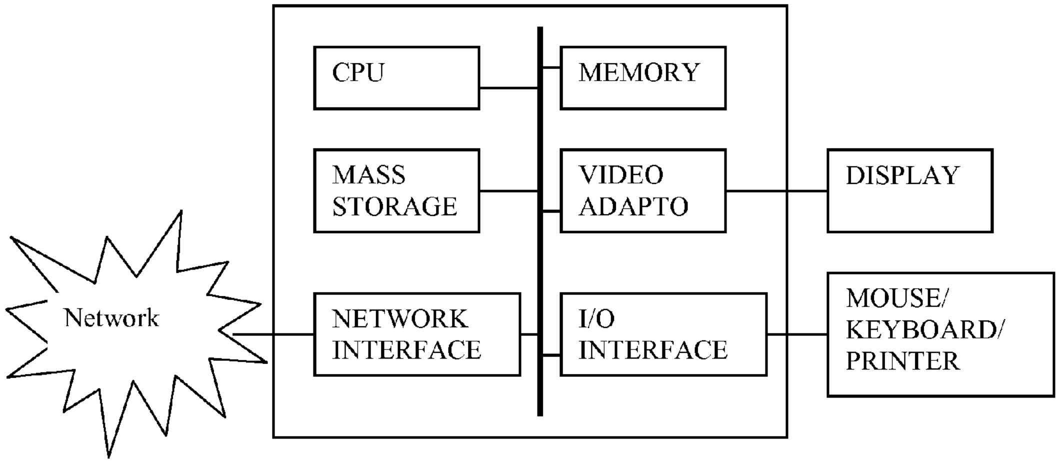
FIG. 10 illustrates a block diagram of a processing system that may be used for implementing the devices and methods disclosed herein.

FIG. 10 illustrates a block diagram of a processing system that may be used for implementing the devices and methods disclosed herein. Specific devices may utilize all of the components shown, or only a subset of the components, and levels of integration may vary from device to device. Furthermore, a device may contain multiple instances of a component, such as multiple processing units, processors, memories, transmitters, receivers, etc. The processing system may comprise a processing unit equipped with one or more input/output devices, such as a speaker, microphone, mouse, touchscreen, keypad, keyboard, printer, display, and the like. The processing unit may include a central processing unit (CPU), memory, a mass storage device, a video adapter, and an I/O interface connected to a bus.

The bus may be one or more of any type of several bus architectures including a memory bus or memory controller, a peripheral bus, video bus, or the like. The CPU may comprise any type of electronic data processor. The memory may comprise any type of system memory such as static random access memory (SRAM), dynamic random access memory (DRAM), synchronous DRAM (SDRAM), read-only memory (ROM), a combination thereof, or the like. In an embodiment, the memory may include ROM for use at boot-up, and DRAM for program and data storage for use while executing programs.

The mass storage device may comprise any type of storage device configured to store data, programs, and other information and to make the data, programs, and other information accessible via the bus. The mass storage device may comprise, for example, one or more of a solid state drive, hard disk drive, a magnetic disk drive, an optical disk drive, or the like.

The video adapter and the I/O interface provide interfaces to couple external input and output devices to the processing unit. As illustrated, examples of input and output devices include the display coupled to the video adapter and the mouse/keyboard/printer coupled to the I/O interface. Other devices may be coupled to the processing unit, and additional or fewer interface cards may be utilized. For example, a serial interface such as Universal Serial Bus (USB) (not shown) may be used to provide an interface for a printer.

The processing unit also includes one or more network interfaces, which may comprise wired links, such as an Ethernet cable or the like, and/or wireless links to access nodes or different networks. The network interface allows the processing unit to communicate with remote units via the networks. For example, the network interface may provide wireless communication via one or more transmitters/transmit antennas and one or more receivers/receive antennas. In an embodiment, the processing unit is coupled to a local-area network or a wide-area network for data processing and communications with remote devices, such as other processing units, the Internet, remote storage facilities, or the like.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. For example, various embodiments described above may be combined with each other.

Although the present invention and its advantages have been described in detail, it should be understood that various changes, substitutions and alterations can be made herein without departing from the spirit and scope of the invention as defined by the appended claims. For example, many of the features and functions discussed above can be implemented in software, hardware, or firmware, or a combination thereof. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method for cancelling or reducing noise or interference component signal in speech signal enhancement processing, the method comprising:

estimating the noise or interference component signal by subtracting voice component signal in an input signal from a first microphone of a cellular or mobile telephone wherein the voice component signal is evaluated as a replica voice component signal produced by passing another input signal from a second microphone of the cellular or mobile telephone through an adaptive filter;

estimating a stepsize which controls adaptive update of the adaptive filter, wherein the stepsize, $0 \leq \text{stepsize} \leq 1$, controls the update amount at each time index, and the stepsize is evaluated by combining an open-loop approach and a closed-loop approach, wherein the open-loop approach comprises using voice/noise/interference classification and SNR estimation in voice area, and the closed-loop approach comprises using a normalized correlation between the replica voice component signal and the input signal from the first microphone, wherein the combining of the open-loop approach and the closed-loop approach comprising generating an initial stepsize estimation for controlling the adaptive filter with the open-loop approach and limiting the estimated stepsize for controlling the adaptive filter with the closed-loop approach;

obtaining a noise or interference reduced speech signal, which is from a target signal of the first microphone or the second microphone, by using the estimated noise or interference component signal;

outputting the noise or interference reduced signal to a speech encoder of the cellular or mobile telephone for telecommunication application.

2. The method of claim 1, wherein cancelling or reducing the noise or interference component signal is based on a beamforming principle.

3. The method of claim 1, wherein the noise or interference component signal is unstable.

4. The method of claim 1, wherein the normalized correlation between the replica voice component signal and the input signal from the first microphone is smoothed and used as one of the parameters for limiting the estimated stepsize value.

5. A speech enhancement processing apparatus comprising:

a processor; and a non-transitory computer readable storage medium storing programming for execution by the processor, the programming including instructions to:

estimate a noise or interference component signal by subtracting voice component signal in an input signal from a first microphone of a cellular or mobile telephone wherein the voice component signal is evaluated as a replica signal produced by passing another input signal from a second microphone of the cellular or mobile telephone through an adaptive filter;

estimate a stepsize which controls adaptive update of the adaptive filter, wherein the stepsize, $0 \leq \text{stepsize} \leq 1$, controls the update amount at each time index, and the stepsize is evaluated by combining an open-loop approach and a closed-loop approach, wherein the open-loop approach comprises using voice/noise/interference classification and SNR estimation in voice area, and the closed-loop approach comprises using a normalized correlation between the replica signal and the input signal from the first microphone, wherein the combine of the open-loop approach and the closed-loop approach comprising generating an initial stepsize estimation for controlling the adaptive filter with the open-loop approach and limiting the estimated stepsize for controlling the adaptive filter with the closed-loop approach;

obtaining a noise or interference reduced speech signal, which is from a target signal of the first microphone or the second microphone, by using the estimated noise or interference component signal;

output the noise or interference reduced signal to a speech encoder of the cellular or mobile telephone for telecommunication application.

6. The method of claim 5, wherein cancelling or reducing the noise or interference component signal is based on a beamforming principle.

7. The method of claim 5, wherein the noise or interference component signal is unstable.

8. The method of claim 5, wherein the normalized correlation between the replica voice component signal and the input signal from the first microphone is smoothed and used as one of the parameters for limiting the estimated stepsize value.

* * * * *